United States Patent
Brandenstein et al.

(10) Patent No.: US 7,429,134 B2
(45) Date of Patent: Sep. 30, 2008

(54) BEARING ARRANGEMENT FOR MEDICAL DEVICE

(75) Inventors: Manfred Brandenstein, Eußenheim (DE); Heinz Breunig, Aschaffenburg (DE); Jurgen Neder, Schweinfurt (DE); Gunter Neder, Schweinfurt (DE); Armin Olschewski, Schweinfurt (DE)

(73) Assignee: AB SKF, Gothenburg (SE)

( * ) Notice: Subject to any disclaimer, the term of this patent is extended or adjusted under 35 U.S.C. 154(b) by 307 days.

(21) Appl. No.: 11/313,672

(22) Filed: Dec. 22, 2005

(65) Prior Publication Data

US 2006/0171623 A1    Aug. 3, 2006

(30) Foreign Application Priority Data

Dec. 23, 2004    (DE) ........................ 10 2004 062 117

(51) Int. Cl.
*F16C 33/58*    (2006.01)
*F16C 43/04*    (2006.01)
*F16C 27/00*    (2006.01)

(52) U.S. Cl. ................. 384/538; 384/537; 384/535

(58) Field of Classification Search ......... 385/535–539, 385/490–492, 448, 485, 518, 542, 99, 110, 385/564–569; 277/375, 408, 431–432; 428/217, 428/698; 148/319, 906; 411/339; 464/68.41; 248/634–635
See application file for complete search history.

(56) References Cited

U.S. PATENT DOCUMENTS

| | | | |
|---|---|---|---|
| 1,219,978 A | | 3/1917 | Masters |
| 2,414,335 A | | 1/1947 | Schroeder |
| 3,142,520 A | * | 7/1964 | Mueller ................ 384/485 |
| 3,460,873 A | * | 8/1969 | Roney ................. 384/535 |
| 3,807,820 A | * | 4/1974 | Schuhmann ............. 384/538 |
| 4,093,859 A | * | 6/1978 | Davis et al. .............. 378/7 |
| 4,453,783 A | * | 6/1984 | Davis et al. ............. 384/99 |
| 4,639,150 A | | 1/1987 | Habermann |
| 4,664,536 A | * | 5/1987 | Kamman ................ 384/99 |
| 4,890,709 A | * | 1/1990 | Reik et al. ............. 192/70.17 |
| 5,137,400 A | * | 8/1992 | Sagara et al. ............ 409/231 |
| 5,174,661 A | * | 12/1992 | Nicolas et al. ........... 384/538 |
| 5,564,903 A | | 10/1996 | Eccles et al. |
| 5,868,503 A | | 2/1999 | Bade |
| 6,210,103 B1 | * | 4/2001 | Ramsay ................ 384/448 |

(Continued)

FOREIGN PATENT DOCUMENTS

DE    69 05 044 U    2/1969

(Continued)

OTHER PUBLICATIONS

German Official Action and English language translation.

*Primary Examiner*—Marcus Charles
(74) *Attorney, Agent, or Firm*—Buchanan Ingersoll & Rooney PC

(57) ABSTRACT

A bearing arrangement used in a medical device in which a rotating component is supported relative to a stationary housing includes a bearing comprising an inner ring and an outer ring, with the inner ring being connected to the component which is to be supported and the outer ring being connected to the housing. To increase quiet running of the rotating component, the connection between the inner ring and the component to be supported and/or between the outer ring and the housing is produced by an annular element which is made of plastic.

20 Claims, 3 Drawing Sheets

U.S. PATENT DOCUMENTS

| | | | |
|---|---|---|---|
| 6,227,715 B1 * | 5/2001 | Erhardt et al. | 384/518 |
| 6,880,977 B2 * | 4/2005 | Seufert | 384/446 |
| 7,278,840 B2 * | 10/2007 | Oehman, Jr. | 384/152 |
| 2005/0053318 A1 * | 3/2005 | Casey | 384/538 |

FOREIGN PATENT DOCUMENTS

| | | |
|---|---|---|
| DE | OS 15 75 635 | 2/1970 |
| DE | 70 18 297 U | 8/1970 |
| DE | 71 22 114 U | 2/1972 |
| DE | 7147440 | 3/1972 |
| DE | 21 43 581 | 11/1972 |
| DE | 25 55 021 C2 | 6/1977 |
| DE | 30 32 820 C2 | 4/1982 |
| DE | 33 16 409 C2 | 11/1984 |
| DE | 35 11 480 C1 | 3/1985 |
| DE | 695 07 576 T2 | 11/1995 |
| DE | 196 45 530 C2 | 5/1998 |
| DE | 200 11 947 U1 | 1/2001 |
| DE | 10235287 A1 * | 2/2004 |
| DE | 10235290 A1 * | 2/2004 |
| FR | 1 296 932 | 8/1961 |
| FR | 2703415 A1 * | 10/1994 |
| GB | 2 082 525 A | 3/1982 |
| JP | 02172446 A * | 7/1990 |
| JP | 2004237103 A * | 8/2004 |
| NL | DD-PS 78 523 | 2/1970 |
| WO | WO 02/27203 A1 | 4/2002 |

* cited by examiner

BEARING ARRANGEMENT FOR MEDICAL DEVICE

CROSS REFERENCE TO RELATED APPLICATION

This application is based on and claims priority under 35 U.S.C. § 119(a) with respect to German Application No. 10 2004 062 117.9 filed on Dec. 23, 2004, the entire content of which is incorporated herein by reference.

FIELD OF THE INVENTION

The invention generally relates to a bearing arrangement. More specifically, the invention pertains to a bearing arrangement for a medical device, with which a rotating component is supported relative to a stationary housing, and wherein the bearing arrangement comprises a bearing with an inner ring connected to the component which is to be supported and an outer ring connected to the housing. The disclosed bearing arrangement has particularly useful application in computer tomographs.

BACKGROUND DISCUSSION

In the case of computer tomographs in particular, it is necessary to support a drum-shaped body relative to the housing such that it can be turned around an axis of rotation for purposes of preparation of tomographic images. To irradiate a patient who is to be examined, an x-ray tube is placed in the drum-shaped body and on the side of the drum diametrically opposite the x-ray tube, radiation detectors which receive the emitted x-radiation are provided.

A bearing arrangement described in the context of an electrical machine is disclosed in DE-OS 15 75 635. Here the outer ring of the bearing is connected to the housing or the frame by way of a damping element or by way of several damping elements which are arranged in a uniformly distributed manner over the periphery of the outer bearing ring. The inner ring of the bearing carries the turning component.

Other publications such as DD-PS 78 523, DE 25 55 021 C2 and DE 30 32 820 C2 disclose bearings for diverse applications in which elastomer blocks or sleeves consisting of elastomer material are used to impart an improved damping property to the bearing.

A roller bearing for a nuclear spin tomograph with magnetic roll bodies and with an inner ring and outer ring between which the roll bodies can roll is described in WO 02/27203 A1. This document describes that the outer ring is surrounded by a nonmagnetic ring.

For computer tomographic systems, bearing arrangements are known in which wire bearings with inserted damping elements are used. Therefore the rotary drum is supported there by way of a ball bearing with traverse wires, the traverse wires being placed in damping plastic inserts. In addition, ceramic balls are used as the roll bodies for the bearing.

It has been found that existing bearing systems especially in computer tomographs still do not meet necessary or desired requirements because the bearing arrangement in operation (when the drum is turning) has relatively high noise development. It is thus hardly possible to meet the requirement for a quiet bearing which produces at most 55 dB(A). The damping of the bearing arrangement therefore has been inadequate for a long time.

Another problem also linked to noise development is that the rotating drum in operation has a not inconsiderable ovalness. That is, the bearing has not been able to grip and support the drum such that it retains a largely round shape.

SUMMARY

An aspect of the invention involves a bearing arrangement in a medical device in which a rotating component is supported relative to a stationary housing. The bearing arrangement comprises a bearing that includes an inner bearing ring and an outer bearing ring, with the inner bearing ring being connected to the component which is to be supported and the outer ring being connected to the housing. At least one of the connection between the inner bearing ring and the component to be supported and the connection between the outer bearing ring and the housing is achieved by an annular element made of plastic.

Preferably, the plastic forming the annular element is a thermoplastic elastomer (TPE). Here the thermoplastic elastomer can be a block copolymer, especially a styrene-block copolymer, a thermoplastic copolyester elastomer, a thermoplastic polyurethane elastomer or a polyether block amide. Alternatively the thermoplastic elastomer can be an elastomer alloy, and especially a thermoplastic polyolefin with an uncrosslinked elastomer phase or a thermoplastic vulcanizate with a chemically crosslinked elastomer portion.

One development involves the annular element being located solely between the inner bearing ring and the component which is to be supported. It is especially advantageous if the annular element on its side facing the bearing ring is conically shaped, with the surface of the bearing ring in contact with the annular element having a corresponding conical shape. The cone angle of the annular element and of the bearing ring is preferably between 2° and 8°. In addition, it is possible to provide a mechanism for axially moving and fixing the bearing ring relative to the annular element. With this mechanism, the prestress in the bearing can be set.

The annular element can be formed by individual segments bordering one another in the peripheral direction. Furthermore, axial fixing of the annular element can be achieved by its being located in an annular groove in the component which is to be supported.

A further improvement of the damping behavior can be achieved by providing the annular element in its area which makes contact with the bearing ring at least one groove in which an O-ring is located.

To improve the concentricity of the part to be supported, both the inner ring and also the outer ring are preferably made as integral one-piece elements. The bearing rings preferably possess an essentially hollow cylindrical base contour, with the extension of the outer ring in the radial direction being at least twice, preferably at least three times, the extension of the inner ring in the radial direction. The extension of the inner ring in the radial direction can be between 15 mm and 30 mm, while the inside diameter of the inner ring in the proposed preferred application is between 1000 and 2000 mm.

The component which is to be supported can be made drum-shaped and can have an inherent stiffness which is low relative to the stiffness of the outer ring of the bearing.

The bearing is advantageously made as a roller bearing in which roll bodies are located between the inner ring and outer ring. Preferably, it is naturally provided that the inner ring, outer ring, and the roll bodies located in between are subject to tolerances such that there is prestress in the bearing.

The indicated development is therefore aimed at the tomograph drum, which has relatively low inherent stiffness, being gripped by the thin-walled inner ring of the bearing, with relatively high roundness being imparted to the inner ring by the outer ring which is made stiff in relation and as a result also to the drum so that quiet running of the bearing arrangement can be realized.

The presence of sufficient prestress in the bearing benefits the centering action which the outer ring of the bearing (which outer ring is made relatively solid) applies to the drum (which has relatively little inherent stiffness) by way of the roll bodies and the inner ring.

The outer ring can furthermore be connected to the housing by way of at least one damping element which impedes the transmission of disruptive vibrations. A number of damping elements can be provided which are arranged or distributed equidistantly over the periphery of the outer ring.

In one preferred form, the outer ring is fixed on the housing by fasteners, especially screws, that extend in the axial direction through the outer ring, the damping element or damping elements and the housing.

The damping element can consist of rubber or of elastomer material, especially of thermoplastic or duroplastic. The bearing rings can be made of nonmagnetic material.

The intended material for the annular element, particularly when used in medical devices, especially computer tomographs, has been found quite surprisingly to lead to very good damping behavior of the bearing arrangement so that the tomograph runs relatively quietly. Thus, the disclosed bearing arrangement is particularly quiet and is also capable of providing relatively uniform running. This is particularly advantageous when the bearing arrangement is used in a computer tomograph, although the bearing arrangement is not limited in that regard. The bearing arrangement, especially for parts which are to be supported and which have relatively low inherent stiffness, should ensure good concentricity and thus contribute to increased quiet running.

BRIEF DESCRIPTION OF THE DRAWING FIGURES

The foregoing and additional features and characteristics of the disclosed subject matter will become more apparent from the following detailed description considered with reference to the accompanying drawing figures in which like reference numerals designate like elements.

DETAILED DESCRIPTION

Figure 1:
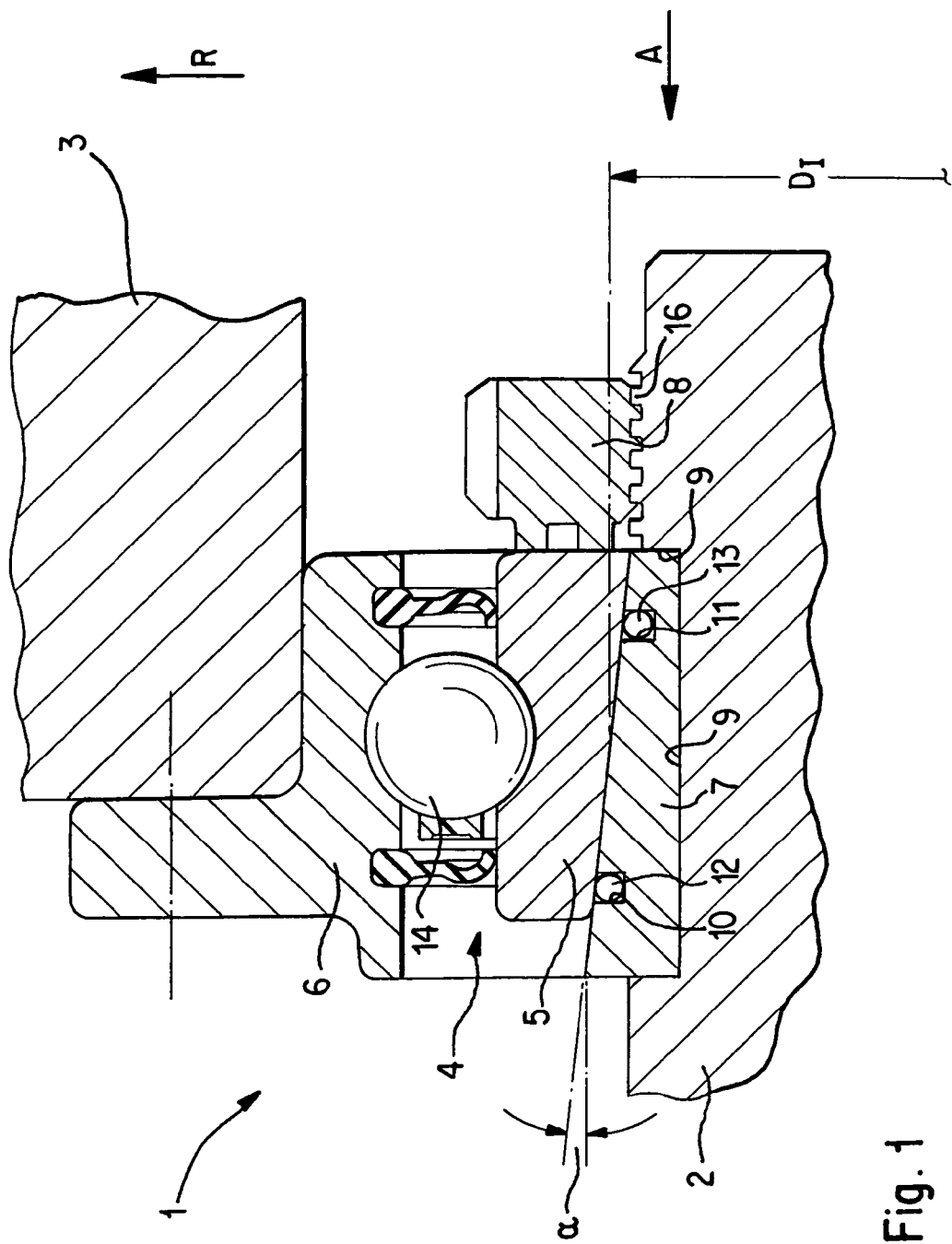
FIG. 1 is a radial cross-section through the top half of the bearing arrangement disclosed herein as used in a computer tomography.

Referring to FIG. 1, the bearing arrangement 1 disclosed herein supports a rotating component 2 in the form of the drum of a computer tomograph relative to the stationary housing 3. The component 2 is relatively thin-walled for weight consideration purposes and so it tends slightly to exhibit or experience unwanted ovalness. The component which is to be supported is drum-shaped and possesses an inherent stiffness which is low relative to the stiffness of the outer bearing ring.

The component 2 is supported by a bearing 4 which is made here as a single-row deep groove ball bearing. However, it is also possible to use other bearing types. The bearing 4 has an inner bearing ring 5 and outer bearing ring 6 between which are positioned a plurality of roll bodies 14 in the form of balls in a known manner. Depending on requirements, the balls 14 consist either of steel or of ceramic. The bearing can be designed such that the inner bearing ring 5, the outer bearing ring and the roll bodies 14 located in between are subject to tolerances such that there is prestress in the bearing 4. The inner and outer bearing rings 5, 6 are preferably made of nonmagnetic material.

As the FIG. 1 cross-section shows, both the inner bearing ring 5 and also the outer bearing ring 6 are made as integral one-piece elements. That is, they each consist of a one-piece ring. Here the entire bearing 4 is made as a so-called heavy bearing in which the outside diameter of the outer ring 6 is greater than roughly 400 mm. Both the inner bearing ring 5 and also the outer bearing ring 6 possess an essentially hollow cylindrical base contour. In addition, the extension of the outer bearing ring 6 in the radial direction R is at least twice, preferably at least three times, the extension of the inner bearing ring 5 in the radial direction R.

In the illustrated embodiment, the radial extension (thickness), in the radial direction R, of the inner ring 5 is roughly 15 mm to 30 mm, while the inside diameter DI of the inner ring 5 is between 1000 mm and 2000 mm.

As illustrated in FIG. 1, the radially inner side or inner surface of the inner ring 5 is conical in shape. That is, the inner surface is tapered so that the inside diameter of the inner ring is larger at the one end (i.e., the left end as seen with reference to FIG. 1) than the other end. In the illustrated embodiment, the inner surface of the inner bearing ring tapers continuously from one end of the inner bearing ring to the opposite end. The cone angle α of the conically shaped inner surface (i.e., the angle of the conically shaped inner surface of the inner bearing ring relative to the axis of the inner bearing ring) is between 2° and 8°, preferably roughly 4°. Between the inner ring 5 and the rotating component 2 there is an annular element 7 which on its radially outer side or outer surface is likewise conical, corresponding to the cone angle of the inner ring 5. In the illustrated embodiment, the annular element 7 is located solely or entirely between the inner bearing ring 5 and the component 2 which is to be supported.

Figure 3:
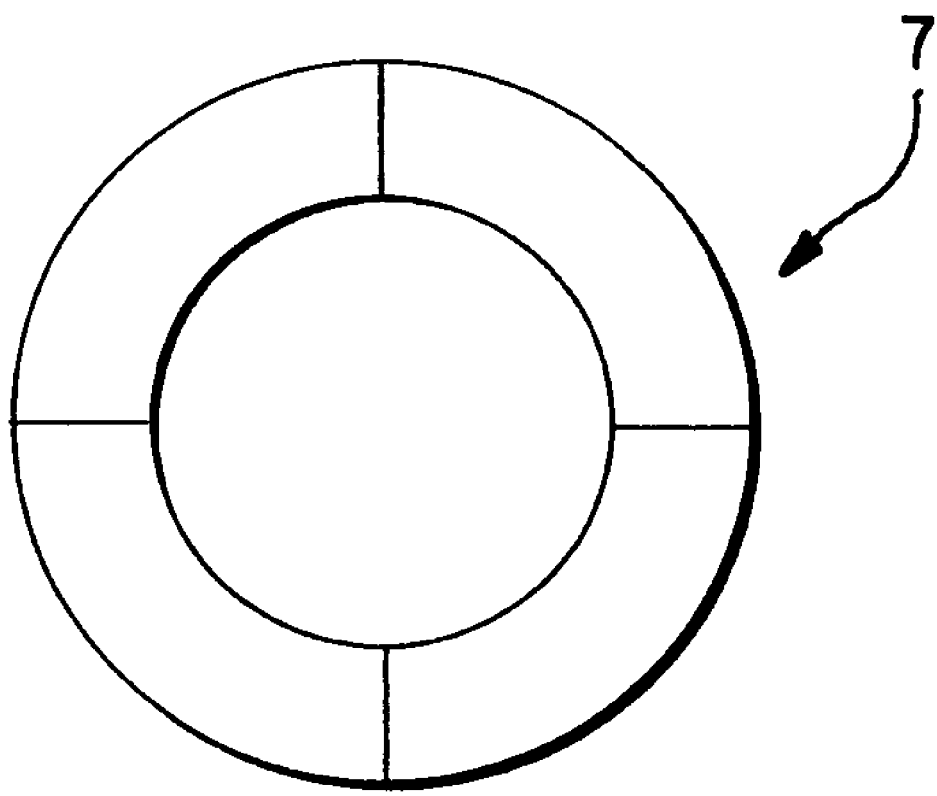
FIG. 3 is an end view of the annular element forming a part of the bearing arrangement, illustrating one possible form of the annular element comprising four separate segments.

The annular element 7 is positioned in a groove 9 formed in the outer surface of the component 2. To make this possible while also facilitating its installation, the annular element 7 can be formed of several segments (as indicated by the dotted outline in FIG. 1) which are combined and border one another over the periphery of the component 2. FIG. 3 illustrates an example of an annular element 7 formed by four separate segments.

A shaft nut 8 is screwed onto a thread 16 formed on the outer periphery of the component. This shaft nut 8 functions as, and constitutes one example of, a means for axially adjusting the inner ring 5 in the axial direction A relative to the annular element 7, and fixing the inner ring at a desired axial position. The prestress force of the entire bearing arrangement can thus be influenced.

In the illustrated and disclosed embodiment, two grooves 10, 11 are machined at axially offset positions (i.e., axially spaced apart from one another) into the outer surface of the annular element 7. The grooves are formed in the area of the annular element 7 which makes contact with the inner bearing ring 5. One rubber O-ring 12, 13 is positioned in each of the grooves 10, 11.

Figure 2:
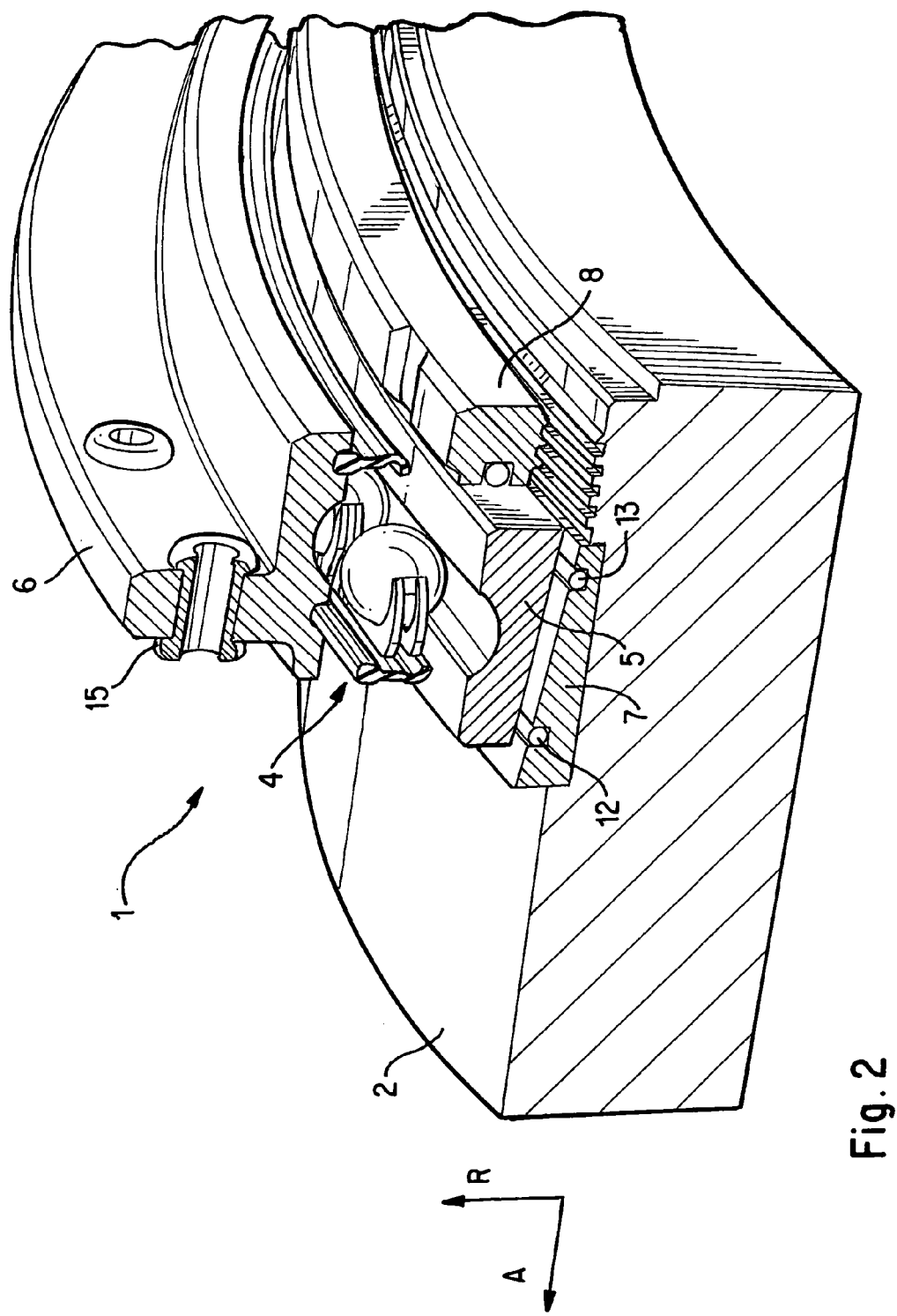
FIG. 2 is a perspective view of a portion of the bearing arrangement shown in FIG. 1 with partially cutaway parts.

The outer ring 6 of the bearing is attached to the housing 3, as shown in FIG. 2, by way of damping elements 15. The damping elements are preferably arranged so as to be distributed equidistantly over the periphery of the outer bearing ring. In this disclosed embodiment, the damping elements 15 are in the form of rubber sleeves or plastic sleeves which are placed in respective holes in the outer ring 6 as shown in FIG.

2. Fastening screws for screwing the outer bearing ring 6 to the housing 3 are inserted into the holes and through rubber or plastic sleeves.

The choice of the material of the annular element 7 has special importance. Here the annular element 7 is made of plastic material, preferably solely plastic material. In a preferred version, thermoplastic elastomer is used as the plastic forming the annular element 7.

Thermoplastic elastomers (TPE) with their properties lie between thermoplastics and elastomers (rubber materials) such that the positive properties of the two material groups are combined. On the one hand, relatively high mechanical stiffnesses can be achieved. On the other hand, the damping behavior of the material is very good.

Like thermoplastics, thermoplastic elastomers also become plastic when heat is applied and harden again when cooled. In contrast to chemical crosslinking in elastomers, in thermoplastic elastomers it is physical crosslinking which is also reversible again by repeated delivery of heat.

According to one configuration of the bearing arrangement, the thermoplastic elastomers are block copolymers which are formed from blocks of different hardness stages. Representatives here are styrene-block copolymers (TPE-S), thermoplastic copolyester elastomers (TPE-E), thermoplastic polyurethane elastomers (TPE-U) or polyether block amides (TPE-A).

Elastomer alloys can also be used which consist of two-phase systems in which the cross-linked or uncrosslinked elastomer particles are mixed in a thermoplastic matrix. Representative materials here are thermoplastic olefins with an uncrosslinked elastomer phase (TPE-O) and thermoplastic vulcanizates with a chemically cross-linked elastomer portion (TPE-V).

To achieve optimum noise reduction, the roll body tracks in the outer and inner ring after grinding can be honed or tumbled. That is, after grinding, a further precision machining is carried out in order to achieve the best possible results.

As noted, the bearing arrangement here is characterized by especially quiet running. When applied to computer tomographs, noise development by the bearing arrangement of less than 55 dB(A) is possible. Also, the drum of the tomograph to be supported is held well centered by the bearing arrangement so that the ovalness of the drum is relatively low. Nevertheless optimum damping of the system is achieved. The vibrations acting on the system both in the axial and also the radial direction are well damped.

The principles, preferred embodiment and manners of use of the present invention have been described in the foregoing specification. However, the invention which is intended to be protected is not to be construed as limited to the particular embodiment disclosed. Further, the embodiment described herein is to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims, be embraced thereby.

What is claimed is:

1. Bearing arrangement in a computer tomograph in which a rotating component is supported relative to a stationary housing, the bearing arrangement comprising a bearing that comprises an inner bearing ring and an outer bearing ring, the inner bearing ring being connected to the component which is to be supported and the outer ring being connected to the housing, at least one of the connection between the inner bearing ring and the component to be supported and the connection between the outer bearing ring and the housing being achieved by an annular element made of plastic;

the annular element possesses a surface facing towards and in contact with a surface of one of the inner bearing ring and the outer bearing ring, said surface of the annular element being conically shaped, the surface of the one of the inner bearing ring and the outer bearing ring that is in contact with the surface of the annular element possessing a conical shape corresponding to the conically shaped surface of the annular element; and means for axially moving said one of the inner bearing ring and the outer bearing ring relative to the annular element and fixing said one of the inner bearing ring and the outer bearing ring relative to the annular element;

wherein the plastic is a thermoplastic elastomer; and wherein the annular element is located in an annular groove in the component which is to be supported.

2. Bearing arrangement in a computer tomograph according to claim 1, wherein the thermoplastic elastomer is a block copolymer.

3. Bearing arrangement in a computer tomograph according to claim 1, wherein the thermoplastic elastomer is one of a styrene-block copolymer, a thermoplastic copolyester elastomer, a thermoplastic polyurethane elastomer and a polyether block amide.

4. Bearing arrangement in a computer tomograph according to claim 1, wherein the thermoplastic elastomer is an elastomer alloy.

5. Bearing arrangement in a computer tomograph according to claim 1, wherein the thermoplastic elastomer is a thermoplastic polyolefin with an uncrosslinked elastomer phase or a thermoplastic vulcanizate with a chemically crosslinked elastomer portion.

6. Bearing arrangement in a computer tomograph according to claim 1, wherein the annular element is located solely between the inner bearing ring and the component which is to be supported.

7. Bearing arrangement in a computer tomograph according to claim 1, wherein the conically shaped surface of the annular element possesses an cone angle of between 2° and 8°.

8. Bearing arrangement in a computer tomograph according to claim 1, wherein the annular element is formed by a plurality of individual segments bordering one another along a periphery of the component which is to be supported.

9. Bearing arrangement in a computer tomograph according to claim 1, wherein the annular element contacts one of the inner bearing ring and the outer bearing ring, an area of the annular element which makes contact with the one of the inner bearing ring and the outer bearing ring being provided with at least one groove in which is positioned an O-ring.

10. Bearing arrangement in a computer tomograph according to claim 1, wherein both the inner bearing ring and the outer ring are integral one-piece elements and possess a hollow cylindrical contour, the outer bearing ring extending in the radial direction by at least twice as much as the inner bearing ring extends in the radial direction.

11. Bearing arrangement in a computer tomograph according to claim 1, wherein the inner bearing ring in the radial direction is between 15 mm and 30 mm, and an inside diameter of the inner bearing ring is between 1000 mm and 2000 mm.

12. Bearing arrangement in a computer tomograph according to claim 1, wherein the component which is to be supported is drum-shaped and possesses a stiffness which is low relative to the stiffness of the outer bearing ring.

13. Bearing arrangement in a computer tomograph according to claim 1, wherein the bearing is a roller bearing with roll bodies positioned between the inner bearing ring and the outer bearing ring.

14. Bearing arrangement in a computer tomograph according to claim 13, wherein the inner bearing ring, the outer bearing ring and the roll bodies are subject to tolerances such that there is prestress in the bearing.

15. Bearing arrangement in a computer tomograph according to claim 1, wherein the outer ring is connected to the housing by way of at least one damping element.

16. Bearing arrangement in a computer tomograph according to claim 15, wherein the at least one damping element comprises a plurality of damping elements distributed equidistantly over a periphery of the outer bearing ring.

17. Bearing arrangement in a computer tomograph according to claim 15, wherein the damping element is made of rubber or of an elastomer material.

18. Bearing arrangement in a computer tomograph according to claim 15, wherein the damping element is made of thermoplastic or duroplastic.

19. Bearing arrangement in a computer tomograph according to claim 1, wherein the inner and outer bearing rings are made of nonmagnetic material.

20. A bearing arrangement forming part of a computer tomograph to support a drum of the computer tomograph relative to a housing, the bearing arrangement comprising:
   an inner bearing ring connected to the drum;
   an outer bearing ring connected to the housing;
   a plurality of roll bodies positioned between the inner bearing ring and the outer bearing ring;
   the inner bearing ring being connected to the drum by way of an annular element;
   the annular element being in contact with the drum and a surface of the inner bearing ring, and being positioned between facing surfaces of the drum and the inner bearing ring; and
   the annular element being made of a thermoplastic elastomer material
   the annular element possessing a conically shaped surface, the surface of the inner bearing ring that is in contact with the surface of the annular element possessing a conical shape corresponding to the conically shaped surface of the annular element; and
   means for axially moving the inner bearing ring relative to the annular element and fixing said inner bearing ring relative to the annular element;
   wherein the annular element is located in an annular groove in the drum.

\* \* \* \* \*